United States Patent
Li et al.

(10) Patent No.: US 6,174,521 B1
(45) Date of Patent: *Jan. 16, 2001

(54) GEL DEODORANT COMPOSITIONS HAVING REDUCED SKIN IRRITATION

(75) Inventors: Li Li, Guangzhou (CN); Norma Dimaculangan Alava, Cincinnati, OH (US); Curtis Bobby Motley, West Chester, OH (US); David Frederick Swaile, Cincinnati, OH (US); Gerald John Guskey, Montgomery, OH (US); Thomas Vincent Orr, Cincinnati, OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/071,100

(22) Filed: May 1, 1998

(51) Int. Cl.[7] ............... A61K 7/32; A61K 7/34; A61K 7/36; A61K 7/38; A61K 7/00
(52) U.S. Cl. .............. 424/65; 424/66; 424/67; 424/68; 424/400; 424/401; 424/DIG. 5
(58) Field of Search ............... 424/65, 66, 67, 424/68, 400, 401, DIG. 5

(56) References Cited

U.S. PATENT DOCUMENTS

| 4,518,582 | 5/1985 | Schamper et al. ............ 424/66 |
| 4,524,062 | * 6/1985 | Laba et al. ............ 424/65 |
| 4,816,261 | 3/1989 | Luebbe et al. ............ 424/65 |
| 5,284,649 | 2/1994 | Juneja ............ 424/67 |
| 5,500,209 | * 3/1996 | Ross et al. ............ 424/66 |

FOREIGN PATENT DOCUMENTS

| 0 089 120 A2 | 9/1983 | (EP) . |
| 0 107 330 A2 | 5/1984 | (EP) . |
| 2 280 111 | 1/1995 | (GB) . |
| WO 97/06778 | 2/1997 | (WO) . |
| WO 97/14398 | 4/1997 | (WO) . |

OTHER PUBLICATIONS

"Acid stable dibenzylidene sorbitol gelled clear solid anti-perspirant formulations: I". Schamper, Jablon Randhawa, Senatore, and Warren. Journal of the Society of Cosmetic Chemists. Jul./Aug. 1986; pp. 225–231.

* cited by examiner

Primary Examiner—Shelley A. Dodson
(74) Attorney, Agent, or Firm—William J. Winter; Lucy Elandjian

(57) ABSTRACT

Disclosed are gel deodorant compositions comprising (a) from about 0.001% to about 50% by weight of a deodorant active, fragrance, or combination thereof; (b) from about 0.01% to about 20% by weight of a gellant; (c) from about 5% to about 90% by weight of a polymeric alcohol having at least one free hydroxyl group and also having from about 2 to about 80 alkoxylate radicals wherein the alkoxylate radical contains from about 2 to about 6 carbon atoms; (d) from about 5% to about 89% by weight of a nonpolymeric alcohol having at least two free hydroxyl groups, and also having from about 4 to about 20 carbon atoms, wherein the weight ratio of the polymeric to nonpolymeric alcohol is from about 18:1 to about 1:5; (e) from zero percent to about 10% by weight of glycerin; and (f) from about 0.01% to about 89% by weight of water. Also disclosed is a method of controlling malodor associated with perspiration by topical application of any deodorant composition containing a select combination of triclosan and triclocarban. All of these compositions remain clear or translucent over extended periods of time, and provide little or no skin irritation in addition to improved cosmetic benefits such as dry feel, ease of application, emolliency, fragrance longevity, and no powdery residue.

21 Claims, No Drawings

GEL DEODORANT COMPOSITIONS HAVING REDUCED SKIN IRRITATION

FIELD OF INVENTION

The present invention relates to gel deodorant compositions which provide reduced skin irritation. In particular, the present invention relates to gel deodorant compositions which contain a gellant, deodorant active or fragrance, and a select combination of a polymeric and nonpolymeric alcohols.

BACKGROUND OF THE INVENTION

Topical deodorants have been formulated in a variety of forms and are intended for topical application to human skin to mask or prevent malodors associated with human perspiration. These topical deodorants are typically applied topically to the underarm or other area of the skin in the form of soft deodorant gels or sticks. These product forms typically contain a gelling agent, solvent, and perfume or antimicrobial active.

Fatty acid soaps are commonly used as gelling agents in topical deodorant gels, examples of which include include sodium or potassium salts of naturally occurring fatty acids. The gelling agent is generally used in combination with a highly polar alcohol solvent to provide aesthetics such as clarity, ease of application, cool and refreshing feel on application, lack of powdery residue, and dry feel. Monohydric and dihydric alcohols, especially propylene glycol and dipropylene glycol, are often used for this purpose.

Many types of gel deodorant formulations are known, including those which comprise fatty acid salts and a solvent such as water, monohydric alcohols, or dihydric alcohols. A typical example of such a formulation are the alcohol-containing gels which comprise a fatty acid salt or other similar gellant, triclosan or other deodorant active, and a polar solvent such as ethanol, propylene glycol, dipropylene glycol or other higher molecular weight polypropylene glycols. Although these alcohol-containing deodorant gels are quite popular and commonly used, many are also harsh to the skin and can cause excessive skin irritation after topical application.

It is therefore an object of the present invention to provide an alcohol-containing gel deodorant composition which is milder to the skin and which causes little or no skin irritation, and further to provide such a composition containing a select ratio a polymeric alcohol and nonpolymeric alcohols. It is a further object of the present to provide such a composition having improved dry feel and other cosmetic benefits such as ease of application, emolliency, fragrance longevity, and/or reduced visible residue.

SUMMARY OF THE INVENTION

The present invention is directed to gel deodorant compositions comprising from about (a) from about 0.001% to about 50% by weight of a deodorant active, fragrance, or combination thereof; (b) from about 0.01% to about 20% by weight of a gellant; (c) from about 5% to about 90% by weight of a polymeric alcohol having at least one free hydroxyl group, and also having from about 2 to about 80 alkoxylate radicals each having from about 2 to about 6 carbon atoms; (d) from about 5% to about 90% by weight of a nonpolymeric alcohol having at least two free hydroxyl groups, and also having from about 3 to about 20 carbon atoms, wherein the weight ratio of the polymeric alcohol to nonpolymeric alcohol is from about 18:1 to about 1:5; (e) from zero percent to about 10% by weight of glycerin; and (f) from about 0.01% to about 89% by weight of water.

It has been found that the gel deodorant compositions of the present invention are milder to the skin and are associated with little or no skin irritation. These compositions also remain substantially clear or translucent over extended periods of time, and provide improved cosmetic benefits such as dry feel, ease of application, emolliency, deodorant efficacy, fragrance longevity, and/or no powdery residue.

DETAILED DESCRIPTION

The gel deodorant compositions of the present invention comprise as essential ingredients a gellant, a polymeric alcohol, an nonpolymeric alcohol, and a perfume and/or deodorant active. These gel deodorant compositions are intended for topical application to the underarm or other suitable areas of the skin. The gel deodorant compositions are preferably in the form of solid or soft solid sticks, but can also be formulated in a variety of non-stick formulations suitable for application to the underarm or other area of the skin.

The term "ambient conditions" as used herein refers to surrounding conditions under about one (1) atmosphere of pressure, at about 50% relative humidity, at about 25° C.

The gel deodorant compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the active level and, therefore, do not include solvents or by-products that may be included in commercially available materials, unless otherwise specified.

Deodorant Active and Fragrance

The gel deodorant composition of the present invention comprises a deodorant active, fragrance or combination thereof, which includes deo-fragrances, at concentrations ranging from about 0.001% to about 50%, preferably from about 0.01% to about 20%, more preferably from about 0.1% to about 10%, by weight of the composition. These deodorant actives and perfumes include any known or otherwise safe and effective deodorant or fragrance suitable for topical application to human skin.

Unless otherwise specified, the term "active" as used herein refers generally to deodorant actives, deo-fragrances or fragrances, whereas the term "deodorant active" specifically refers to topical materials which can prevent or eliminate malodors resulting from perspiration. The term "fragrance" as used herein specifically refers to any topical material which covers or masks malodors resulting from perspiration, or which otherwise provides the composition with the desired perfumed aroma.

a) Deodorant Active

Deodorant actives suitable for use in the gel deodorant composition includes any topical material that is known for or is otherwise effective in preventing or eliminating malodor associated with perspiration. These deodorant actives are typically antimicrobial agents (e.g., antibacterial agents, antifungal agents), malodor-absorbing material, or combinations thereof Preferred deodorant actives are antimicrobial agents, non-limiting examples of which include cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Preferred deodorant actives are triclosan, triclocarban and combinations thereof, wherein the preferred concentration of either triclosan or triclocarban ranges from about 0.01% to about 1.0%, more preferably from about 0.1% to about 0.5%, even more preferably from about 0.1% to 0.3%, by weight of the composition, and wherein the total concentration of triclosan and triclocarban when used together in a composition ranges from about 0.01% to about 2.0%, more preferably from about 0.2% to about 1.0%, even more preferably from about 0.2% to about 0.6%, by weight of the composition. It has been found that the combination of these two deodorant actives provides a deodorant efficacy that exceeds the cumulative deodorant efficacy that one would otherwise predict from such a combination.

The preferred combination of triclosan and triclocarban is effective in providing improved deodorant performance from the deodorant compositions described herein, or from any known deodorant or topical composition containing such a combination that is otherwise suitable for application to human skin. The present invention is therefore also directed to a method of controlling malodor associated with human perspiration by topically applying the triclosan/triclocarban combination described above, or any other suitable composition containing the triclosan/triclocarban combination described above, to the underarm or other area of the skin. From most deodorant compositions containing this combination, from about 0.1 gram to about 2.0 gram per axilla of the deodorant composition is applied, preferably once or twice daily, more preferably once daily.

Other deodorant actives include odor-absorbing materials such as carbonate and bicarbonate salts, including alkali metal carbonates and bicarbonates, ammonium and tetraalkylammonium. Preferred are sodium and potassium salts of such odor-absorbing materials.

The gel deodorant composition is preferably substantially free of astringent antiperspirant actives such as aluminum or zirconium astringent salts or complexes. In this context, the term "substantially free" means that the gel deodorant composition preferably contains less than about 5%, more preferably less than about 2%, most preferably zero percent, by weight of such astringent antiperspirant actives.

b) Fragrance

Fragrances suitable for use in the gel deodorant composition include any topical material that is known for or is otherwise effective in masking malodor associated with perspiration, or which otherwise provides the composition with the desired perfumed aroma. These fragrances include any perfume or perfume chemical suitable for topical application to the skin.

The concentration of the fragrance in the gel deodorant composition should be effective to provide the desired aroma characteristics or to mask malodor, wherein the malodor is inherently associated with the composition itself or is associated with malodor development from human perspiration. Also, the fragrance and whatever carriers accompany it should not impart excessive stinging to the skin, especially broken or irritated skin, at the levels previously disclosed. The fragrance will typically be in the form of water insoluble perfumes that are solubilized in the gel deodorant composition.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. Nos. 4,322,308 and 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76, and Pomeransol 314); aldehydes and ketones (such as B-methyl naphthyl ketone, p-t-butyl-A-methyl hydrocinnamic aldehyde, and p-t-amyl cyclohexanone); polycyclic compounds (such as coumarin and β-naphthyl methyl ether); esters (such as diethyl phthalate, phenylethyl phenylacetate, non-anolide-1:4). Fragrances also include esters and essential oils derived from floral materials and fruits, citrus oils, absolutes, aldehydes, resinoides, musk and other animal notes (e.g., natural isolates of civet, castoreum, and musk), balsamic, etc. and alcohols (such as dimyrcetol, phenylethyl alcohol, and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable fragrances are those which mask or help to mask odors associated with perspiration (hereinafter referred to as odor masking fragrances) or odors associated with the inherent malodor of some gel deodorant compositions or the materials therein. Some nonlimiting examples of suitable odor masking fragrances are described in U.S. Pat. Nos. 5,554,588, 4,278,658, 5,501,805, and EP Patent Application 684 037 A1, which descriptions are incorporated herein by reference. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The fragrance for use herein may also contain solubilizers, diluents, or solvents which are well known in the art. Such materials are described in Arctander, Perfume and Flavour Chemicals (Aroma Chemicals), Vol. I and II (1969). These materials typically include dipropylene glycol, diethylene glycol, $C_1$–$C_6$ alcohols, and benzyl alcohol.

Gellant

The gel deodorant composition of the present invention comprises a gellant suitable for providing the desired hardness and application characteristics to the composition. Gellant concentrations range from about 0.01% to about 20%, preferably from about 0.1% to about 10%, more preferably from about 1% to about 8%, even more preferably from about 3% to about 7%, by weight of the gel deodorant composition.

Any known gellant or gellant system may be used in the gel deodorant composition of the present invention provided that the selected gellants can melt and form a solution or other homogenous liquid or liquid dispersion with the selected solvent system described herein at a processing temperature of from about 50° C. to about 150° C., preferably from about 50° C. to about 120° C., more preferably from about 60° C. to about 100° C. The selected gellant must also provide the gel deodorant composition with the desired gel matrix after formulation and completion of processing which then provides the composition with the desired hardness or spreading characteristics.

Preferred gellants for use in the gel deodorant composition of the present invention are salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, sodium laurate, sodium arachidate, sodium behenate, potassium stearate, potassium palmitate, sodium myristate, potassium palmitate, aluminum monostearate, and combinations thereof. Most preferred is sodium stearate.

Non-limiting examples of fatty acids suitable for making the fatty acid gellants include acids such as myristic, palmitic, stearic, oleic, behenic, arachidic, lauric, linoleic, linolenic, margaric and combinations thereof. These fatty acids are preferably derived from sources such as coconut oil, beef tallow, lanolin, fish oil, beeswax, palm oil, peanut oil, olive oil, cottonseed oil, soybean oil, corn oil, rapeseed oil, rosin acids, greases, and other natural sources, or are derived by synthetic or semisynthetic methods well known to those skilled in the formulation art.

Other suitable gellants suitable for use in the gel deodorant composition include hydroxy acids, fatty acids, esters and amides of fatty acids and fatty acid salts, hydroxy fatty acids, cholesterolic materials, lanolinolic materials, and other amide gellants known for use as gelling agents or which are otherwise described in detail hereinafter.

Nonlimiting examples of suitable fatty acid gellants include fatty acid and hydroxy or alpha hydroxy fatty acids, having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, combinations thereof, and salts thereof.

Other nonlimiting examples of specific gellants suitable for use in the gel deodorant composition include those which correspond to the following formula:

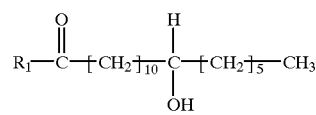

wherein $R_1$ is $OR_2$ or $NR_2R_3$; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof.

Nonlimiting examples of suitable amide gellants for use in the gel deodorant composition include disubstituted or branched monoamide gellants, monosubstituted or branched diamide gellants, triamide gellants, and combinations thereof. Preferred are alkyl amides of di- and/or tri-basic carboxylic acids or anhydrides which conform to the formula:

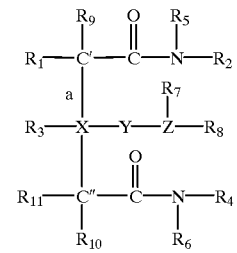

wherein a backbone is formed from the linkage of C', C" and X and wherein
a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;
b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nil, nitrogen, aryl or $-(CH_2)_n-$ where n is an integer from 1 to 6, preferably $-(CH_2)_n-$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
   (i) when X is nil, Y, Z, $R_3$, $R_7$ and $R_8$ are nil, C' is bonded directly to C" and $R_1$ is not a hydrogen;
   (ii) when X and Z are not nil and Y is nil, X is directly bonded to Z;
   (iii) when Z is nil, a hydrogen or a hydroxy, $R_7$ and $R_8$ are nil; and
   (iv) when "a" is a double bond, $R_3$ and $R_9$ are nil.

Nonlimiting examples of specific alkyl amide gellants suitable for use in the gel deodorant composition include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene-1,2,3-trioctylamide, N,N',N"-tri (acetodecylamide)amine, 2-dodecyl-N,N'-dihexylsuccinamide, and 2 dodecyl-N,N'-dibutylsuccinamide.

Polymeric Alcohols

The gel deodorant composition of the present invention comprises a polymeric alcohol in combination with an nonpolymeric alcohol to solubilize the gellant selected for use in the gel deodorant composition. The combination solvent may also be used to solubilize the deodorant active or fragrance. The concentration of the polymeric alcohol in the gel deodorant composition ranges from about 5% to about 90%, preferably from about 5% to about 80%, more preferably from about 10% to about 75%, even more preferably from about 20% to about 60%, by weight of the composition.

The term "polymeric alcohol" as used herein means any alkoxylated alcohol that is liquid under ambient conditions, and which has at least one free hydroxyl group, wherein the polymeric alcohol has from about 1 to about 80, preferably from about 3 to about 20, repeating alkylene oxide radicals, and wherein each of the repeating alkylene oxide radicals has from 2 to 6 carbon atoms.

Nonlimiting examples of polymeric alcohols suitable for use in the gel deodorant composition include diethylene glycol, triethylene glycol, dipropylene glycol, tripropylene glycol, liquid polypropylene polyethylene glycol copolymers, tetrapropylene glycol, tetraethylene glycol, dibutylene glycol, trimethylene glycol, diethylene glycol monoethylether, PEG-8, 1,3-butane diol, 1,4-butane diol, glycerol propoxylate, and mixtures thereof. Preferred polymeric alcohols include dipropylene glycol, tripropylene glycol, tetrapropylene glycol, and mixtures thereof.

As used herein, polyethylene glycols, polypropylene glycols, and polypropylene polyethylene glycol copolymers include alkyl ether derivatives of these compounds (e.g., ethyl, propyl, myristyl, and butyl ether derivatives) provided that all such derivatives have at least one free hydroxyl group. Examples of such compounds are the myristyl ether derivatives of polypropylene glycol, such as PPG-3 myristyl ether.

Nonpolymeric Alcohol

The gel deodorant composition of the present invention comprises a nonpolymeric alcohol as a solvent for the selected gellant or gellant system, and for use in combination with the polymeric alcohol solvent described herein. Concentrations of the nonpolymeric alcohol range from about 5% to about 90%, preferably from about 5% to about 80%, more preferably from about 10% to about 75%, even more preferably from about 20% to about 60%, by weight of the composition.

The gel deodorant composition comprises a nonpolymeric alcohol as defined herein, wherein the weight ratio of the polymeric to nonpolymeric alcohol in the composition ranges from about 18:1 to about 1:5, more preferably from about 7.5:1 to about 1:5, even more preferably from about 4:1 to about 1:2.

The nonpolymeric alcohols suitable for use herein are those which contain at least two free hydroxyl groups, e.g., dihydric or polyhydric, and which have from about 4 to about 20 carbon atoms, preferably from about 4 to about 10 carbon atoms, nonlimiting examples of which include propylene glycol, hexylene glycol, 1,2-hexandiol, 1,3-butylene glycol, 1,2,6-trihydroxyhexane, 1,2,3-trihydroxyhexane, and combinations thereof. More preferred are hexylene glycol, 1,2-hexanediol, or combinations thereof, most preferably 1,2-hexanediol.

The gel deodorant compositions may further comprise other additional solvents, polar or otherwise, some nonlimiting examples of which are described in U.S. Pat. No. 5,429,816; Cosmetics, Science, and Technology, Vol. 1, 27–104, edited by Balsam and Sagarin (1972); U.S. Pat. Nos. 4,202,879; and 4,816,261, which descriptions are incorporated herein by reference.

The gel deodorant compositions of the present invention are preferably substantially free of propylene glycol, dipropylene glycol, or combinations thereof. In this context, the term "substantially free" means that the compositions preferably contain less than 20%, more preferably less than 10%, most preferably zero percent, by weight of propylene glycol, dipropylene glycol, or combinations thereof.

Water

The gel deodorant compositions of the present invention are aqueous systems which comprise from about 0.01% to about 89%, preferably from about 5% to about 50%, more preferably from about 10% to about 30%, of water by weight of the composition.

Glycerin

The gel deodorant compositions of the present invention preferably further comprise glycerin at concentrations of from zero percent to about 10%, preferably from about 0.5% to about 7%, even more preferably from about 1% to about 6%, by weight of the composition.

Optional Ingredients

The gel deodorant compositions of the present invention may further comprise one or more optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants and other personal care compositions, and may also be used in the gel deodorant compositions herein, provided that such optional materials are compatible with the essential materials described herein, or do not otherwise unduly impair product performance.

Nonlimiting examples of optional ingredients suitable for use in the gel deodorant composition herein include pH buffering agents; additional emollients; humectants; soothing agents; dyes and pigments; medicaments; preservatives; and soothing agents such as aloe vera, allantoin, D-panthenol, avocado oil and other vegetative oils, and lichen extract.

Method of Manufacture

The gel deodorant compositions of the present invention may be made by any of the methods known in the art for formulating deodorant gel compositions. As will be apparent to those skilled in the art, the particular method will be dependent upon the selection of the specific types and amounts of the components employed.

In general, the compositions of the present invention can be prepared by mixing the polymeric alcohol, nonpolymeric alcohol, and deodorant active. Gellant is added with agitation and the mixture is heated to a temperature of from about 75° C. to about 100° C. to allow the gellant to melt and form a substantially clear or translucent liquid. The resulting liquid is cooled before adding fragrance (if applicable), and then the cooled composition is poured into an appropriate container or dispenser at about 70° C. and allowed to solidify within the container or dispenser by cooling or allowing to cool the contained composition to ambient temperature.

Method For Use

The gel deodorant composition of the present invention may be topically applied to the skin in any known or otherwise effective method for controlling malodor associated with perspiration. These methods comprise applying to the underarm or other area of the human skin of a safe and effective amount of the gel deodorant composition of the present invention. In this context, the term "safe and effective amount" means an amount of the gel deodorant composition topically applied to the skin which is effective in masking, reducing or eliminating malodor associated with human perspiration while being safe for human use at a reasonable risk/benefit ratio. In this context, a safe and effective amount typically ranges from about 0.1 gram per axilla to about 2.0 gram per axilla. The compositions are preferably applied to the axilla or other area of the skin one or two times daily, preferably once daily.

EXAMPLES

The following examples illustrate specific embodiments of the gel deodorant compositions of the present invention, including methods of manufacture and use, but are not intended to be limiting thereof. Other modifications can be undertaken by the skilled artisan without departing from the spirit and scope of this invention. All of the compositions provide improved application aesthetics and/or low irritation performance. The gel deodorant compositions containing 1,2-hexanediol have improved visual clarity, and the compositions containing the triclosan/triclocarban combination provide improved deodorant efficacy.

Each of the exemplified compositions are prepared by combining all of the listed components, except for the gellant and fragrance where applicable, and heating with agitation the combination of ingredients to a temperature above the melt point of the gellant but less than 100°C. The gellant is then added while continuing to heat and agitate the mixture until a clear single-phase solution results, at which point the mixture is cooled to a temperature of between 65° C. and 80° C. Fragrance is added with agitation to the cooled mixture. The fragrance-containing mixture is then poured into an appropriate dispenser or other container and allowed to solidify by cooling to ambient temperature.

TABLE 1

| Ingredient | \multicolumn{6}{c}{Examples} |
|---|---|---|---|---|---|---|
| | I | II | III | IV | V | VI |
| Butylene Glycol | — | 43.5 | — | — | — | — |
| Dipropylene Glycol | — | — | — | 10 | 10 | 10 |
| Hexylene Glycol | 38.5 | — | — | 10 | 13 | 14.5 |
| Tripropylene Glycol | — | — | — | — | 33.5 | 10 |
| Tetra Propylene Glycol | — | — | 45 | 24.5 | — | — |
| PEG 200 | — | — | — | — | — | 35 |
| PEG 400 | 22 | 10 | 10 | 10 | 10 | — |
| Distilled water | 23 | 22 | 22 | 22 | 20 | 20 |
| Glycerin | 4 | 12 | 12 | 12 | — | — |
| PPG-3 Myristyl Ether | 1.7 | 1.7 | 1 | 1 | 1.135 | 1.135 |
| Triclosan | 0.3 | 0.3 | 0.3 | 0.3 | 0.3 | 0.3 |
| Sodium Bicarbonate | 0.275 | 0.175 | 0.175 | 0.175 | — | — |
| Sodium Hydroxide, 50% Soln. | — | — | — | — | 0.04 | 0.04 |
| Tetrasodium EDTA | 0.025 | 0.025 | 0.025 | 0.025 | 0.025 | 0.025 |
| Sodium Stearate | 5.2 | 5.5 | 5.5 | 5.5 | 7 | 5.5 |

TABLE 1-continued

| Ingredient | Examples | | | | | |
|---|---|---|---|---|---|---|
| | I | II | III | IV | V | VI |
| Fragrance | 5 | 4 | 2.5 | 3 | 3.5 | 2 |
| Color | — | 0.8 | 1.5 | 1.5 | 1.5 | 1.5 |

TABLE 2

| Ingredient | Examples | | | | | |
|---|---|---|---|---|---|---|
| | VII | VIII | IX | X | XI | XII |
| Perfume | 3.5 | 3.5 | 3.5 | 3.5 | 3.5 | 3.5 |
| Triclosan | 0.3 | 0.3 | 0.3 | 0.3 | 0.3 | 0.3 |
| Triclocarban | 0.25 | 0.25 | 0.25 | 0.25 | 0.25 | 0.25 |
| Glycerin | 5.0 | 5.0 | 1.5 | 5.0 | 5.0 | 1.5 |
| Sodium stearate C14–C18 | — | 4.2 | 2.2 | — | 4.2 | 2.2 |
| Sodium stearate C12–C22 | 5.6 | 1.4 | 2.2 | 5.6 | 1.4 | 2.2 |
| Sodium hydroxide | 0.04 | 0.04 | 0.04 | 0.04 | 0.04 | 0.04 |
| Tetrasodium EDTA | 0.025 | 0.025 | 0.025 | 0.025 | 0.025 | 0.025 |
| PPG-5 Ceteth 20 | — | — | 5.0 | — | — | 5.0 |
| PPG-3 Myristyl Ether | 2.535 | 2.535 | 2.535 | 2.535 | 2.535 | 2.535 |
| PEG 400 | 35.75 | 35.75 | 35.0 | 35.75 | 35.75 | 35.0 |
| Hexylene glycol | 20.0 | 20.0 | 20.45 | — | — | — |
| 1,2-hexanediol | — | — | — | 20.0 | 20.0 | 20.45 |
| Distilled water | 27.0 | 27.0 | 27.0 | 27.0 | 27.0 | 27.0 |

The compositions described in Examples I–VI are also formulated with 0.25% triclocarban in place of the 0.3% triclosan. About 0.05% by weight of water is also added to the triclocarban formulations.

What is claimed is:

1. A gel deodorant composition comprising:
   (a) from about 0.001% to about 50% by weight of a deodorant active, fragrance, or combination thereof;
   (b) from about 0.01% to about 20% by weight of a gellant selected from the group consisting of salts of fatty acids, wherein the fatty acid moiety has from about 12 to about 40 carbon atoms, hydroxy acids, esters and amides of fatty acid salts, esters and amides of fatty acids, hydroxy fatty acids, cholesterolic materials, lanolinolic materials, and combinations thereof;
   (c) from about 5% to about 90% by weight of a polymeric alcohol having at least one free hydroxyl group and also having from about 2 to about 80 alkoxylate radicals each having from 2 to 6 carbon atoms;
   (d) from about 5% to about 90% by weight of a nonpolymeric alcohol having at least two free hydroxyl groups and from about 4 to about 20 carbon atoms, wherein the weight ratio of the polymeric to nonpolymeric alcohol is from 18:1 to about 1:5;
   (e) from 0.5% to about 10% by weight of glycerin;
   (f) from about 0.01% to about 89% by weight of water.

2. The composition of claim 1 wherein the gellant is a fatty acid salt having from about 12 to about 22 carbon atoms.

3. The composition of claim 2 wherein the fatty acid salt is selected from the group consisting of sodium stearate, sodium palmitate, sodium myristate, sodium laurate, sodium behenate, sodium arachidate, potassium stearate, potassium palmitate, potassium myristate, and mixtures thereof.

4. The composition of claim 3 wherein the fatty acid salt comprises sodium stearate.

5. The composition of claim 1 wherein the polymeric alcohol is selected from the group consisting of diethylene glycol, triethylene glycol, dipropylene glycol, tripropylene glycol, liquid polypropylene polyethylene glycol copolymers, tetrapropylene glycol, tetraethylene glycol, dibutylene glycol, trimethylene glycol, diethylene glycol monoethylether, PEG-8, glycerol propoxylate, and mixtures thereof.

6. The composition of claim 5 wherein the composition comprises a mixture of two or more polymeric alcohols selected from the group consisting of diethylene glycol, triethylene glycol, dipropylene glycol, tripropylene glycol, liquid polypropylene polyethylene glycol copolymers, tetrapropylene glycol, tetraethylene glycol, dibutylene glycol, trimethylene glycol, diethylene glycol monoethylether, PEG-8, and glycerol propoxylate.

7. The composition of claim 1 wherein the deodorant active is selected from the group consisting of triclocarban, triclosan, and combinations thereof.

8. The composition of claim 7 wherein the composition comprises from about 0.01% to about 1.0% by weight of triclosan and from about 0.01% to about 1.0% by weight of triclocarban.

9. The composition of claim 1 wherein the nonpolymeric alcohol is selected form the group consisting of propylene glycol, hexylene glycol, 1,2-hexanediol, ethylene glycol, butylene glycol, 1,2,6-trihydroxyhexane, 1,2,3-trihydroxyhexane, and mixtures thereof.

10. The composition of claim 9 wherein the nonpolymeric alcohol is selected from the group consisting of hexylene glycol, 1,2-hexanediol, and combinations thereof.

11. A gel deodorant composition comprising:
   (a) from about 0.001% to about 50% by weight of a deodorant active, fragrance, or combination thereof;
   (b) from about 0.01% to about 20% by weight of a gellant selected from the group consisting of salts of fatty acids, wherein the fatty acid moiety has from about 12 to about 40 carbon atoms, hydroxy acids, esters and amides of fatty acid salts, esters and amides of fatty acids, hydroxy fatty acids, cholesterolic materials, lanolinolic materials, and combinations thereof;
   (c) from about 5% to about 90% by weight of a polymeric alcohol having at least one free hydroxyl group and also having from about 2 to about 80 alkoxylate radicals each having from 2 to 6 carbon atoms;
   (d) from about 10% to about 75% by weight of hexylene glycol, wherein the weight ratio of the polymeric to hexylene glycol is from 18:1 to about 1:5;
   (e) from 1 to about 7% by weight of glycerin; from about 0.01% to about 89% by weight of water.

12. The composition of claim 11 wherein the deodorant active is selected from the group consisting of triclocarban, triclosan, and combinations thereof.

13. The composition of claim 12 wherein the composition comprises from about 0.01% to about 1.0% by weight of triclosan and from about 0.01% to about 1.0% by weight of triclocarban.

14. The composition of claim 11 wherein the gellant is a fatty acid salt having from about 12 to about 22 carbon atoms.

15. The composition of claim 14 wherein the fatty acid salt is selected from the group consisting of sodium stearate, sodium palmitate, sodium laurate, sodium behenate, sodium arachidate, sodium myristate, potassium stearate, potassium palmitate, potassium myristate, and mixtures thereof.

16. The composition of claim 15 wherein the fatty acid salt comprises sodium stearate.

17. The composition of claim 14 wherein the polymeric alcohol is selected from the group consisting of diethylene glycol, triethylene glycol, dipropylene glycol, tripropylene glycol, liquid polypropylene polyethylene glycol copolymers, tetrapropylene glycol, tetraethylene glycol, dibutylene glycol, trimethylene glycol, diethylene glycol monoethylether, PEG-8, glycerol propoxylate, and mixtures thereof.

18. The composition of claim 17 wherein the composition comprises two or more of the polymeric alcohols selected from the group consisting of diethylene glycol, triethylene glycol, dipropylene glycol, tripropylene glycol, liquid polypropylene polyethylene glycol copolymers, tetrapropylene glycol, tetraethylene glycol, dibutylene glycol, trimethylene glycol, diethylene glycol monoethylether, PEG-8, glycerol propoxylate, and mixtures thereof.

19. The composition of claim 18 wherein less than 20% by weight of the polymeric alcohol has less than 3 repeating alkoxylate radicals.

20. A method for controlling malodor associated with perspiration by applying to the underarm or other area of the human skin a deodorant composition comprising:

(A) from about 0.01% to about 1.0% by weight of triclosan, and (B) from about 0.01% to about 1.0% by weight of triclocarban.

21. The method of claim 20 wherein the composition comprises from about 0.1% to about 0.3% by weight of triclosan and from about 0.1% to about 0.3% by weight of triclocarban.

* * * * *

UNITED STATES PATENT AND TRADEMARK OFFICE
CERTIFICATE OF CORRECTION

PATENT NO.   : 6,174,521 B1
DATED        : January 16, 2001
INVENTOR(S)  : Li et al.

It is certified that error appears in the above-identified patent and that said Letters Patent is hereby corrected as shown below:

<u>Title page,</u>
Item [*] Notice, delete the phrase "by 0 days" and insert -- by 3 days --

Signed and Sealed this

Twenty-first Day of September, 2004

JON W. DUDAS
*Director of the United States Patent and Trademark Office*